United States Patent
Ma et al.

(10) Patent No.: US 11,938,025 B1
(45) Date of Patent: Mar. 26, 2024

(54) SHEATH FOR LOADING AND RETRACTING PROSTHETIC IMPLANT AND DELIVERY SYSTEM

(71) Applicant: VENUS MEDTECH (HANGZHOU) INC., Zhejiang (CN)

(72) Inventors: Renzheng Ma, Zhejiang (CN); Jianan Wang, Zhejiang (CN); Meirong Liu, Zhejiang (CN); Mingrui Zheng, Zhejiang (CN)

(73) Assignee: VENUS MEDTECH (HANGZHOU) INC., Hangzhou (CN)

( * ) Notice: Subject to any disclaimer, the term of this patent is extended or adjusted under 35 U.S.C. 154(b) by 0 days.

(21) Appl. No.: 18/212,199

(22) Filed: Jun. 21, 2023

Related U.S. Application Data

(63) Continuation of application No. PCT/CN2023/101126, filed on Jun. 19, 2023.

(30) Foreign Application Priority Data

May 9, 2023 (CN) .......................... 202310519624.3

(51) Int. Cl.
*A61F 2/24* (2006.01)
*A61F 2/95* (2013.01)
*A61M 25/00* (2006.01)

(52) U.S. Cl.
CPC .......... *A61F 2/2436* (2013.01); *A61F 2/9517* (2020.05); *A61F 2/9522* (2020.05); *A61M 25/0074* (2013.01)

(58) Field of Classification Search
CPC .............. A61F 2/011; A61F 2002/9534; A61F 2002/9528; A61F 2/2418; A61F 2/2436; A61M 25/0074
See application file for complete search history.

(56) References Cited

U.S. PATENT DOCUMENTS

| | | | | |
|---|---|---|---|---|
| 2008/0033528 | A1* | 2/2008 | Satasiya | A61F 2/915 623/1.15 |
| 2009/0192518 | A1* | 7/2009 | Golden | A61F 2/95 606/108 |
| 2011/0098804 | A1* | 4/2011 | Yeung | A61F 2/2412 623/2.1 |
| 2013/0144328 | A1* | 6/2013 | Weber | A61M 25/0074 606/200 |
| 2022/0395667 | A1* | 12/2022 | Keating | A61M 25/0074 |

FOREIGN PATENT DOCUMENTS

DE 102009046728 A1 * 5/2011 ....... A61B 17/00491

* cited by examiner

*Primary Examiner* — Kelly J Bekker
*Assistant Examiner* — Andrew P. Restaino

(57) ABSTRACT

A sheath for loading and retrieving a prosthetic implant is disclosed, which includes a tube. The tube has opposing distal and proximal ends in its axial direction, and the distal end has a plurality of support rods arranged at intervals in a circumferential direction of the tube and having relative converged and flared configurations. A plurality of connecting strips are provided in the axial direction between two adjacent support rods, and each connecting strip is folded back and forth in the converged configuration and tends to be straightened in the flared configuration relative to the converged configuration. The straightened lengths of the connecting strips increase sequentially from the proximal end to the distal end, and two ends of each connecting strip are connected to the support rods on the corresponding sides and the connecting portions have the same axial level.

18 Claims, 7 Drawing Sheets

SHEATH FOR LOADING AND RETRACTING PROSTHETIC IMPLANT AND DELIVERY SYSTEM

CROSS-REFERENCE TO RELATED APPLICATIONS

The present application is a Continuation Application of PCT Application No. PCT/CN2023/101126, filed on Jun. 19, 2023, which claims priority of Chinese Patent Application No. CN202310519624.3, filed on May 9, 2023, the entire contents of which are hereby incorporated by reference.

TECHNICAL FIELD

The present disclosure relates to the technical field of a medical device, in particular to a sheath for loading and retracting prosthetic implant and a delivery system.

DESCRIPTION OF THE PRIOR ART

A diseased or defected heart valve can be repaired or replaced by implanting a prosthetic heart valve (hereinafter, prosthetic implant). The prosthetic implant is loaded at the distal end of the delivery system, and is delivered to the surgical site by intervention of the delivery system. If the prosthetic implant is improperly positioned within the native valve annulus during the expansion process, serious complications may occur.

The existing method is to recapture the prosthetic implant, that is, to recompress and reposition the completely or partially expanded prosthetic implant into the sheath of the delivery system. This process can also be called the retraction of the prosthetic implant. The term "retraction" and "recapture" here refer to the same meaning. After being retracted, the prosthetic implant is withdrawn outside the human body or repositioned in the human body.

The existing delivery system has the problem of stuck and unsmooth retracting, or the prosthetic implant damaging the sheath, resulting in failure of retraction.

SUMMARY OF THE DISCLOSURE

The present disclosure provides a sheath for loading and retracting a prosthetic implant, which improves the smoothness of retracting the prosthetic implant and avoids damage to the sheath during retraction.

The disclosure provides a sheath for loading and retracting a prosthetic implant, including a tube having opposing distal and proximal ends in its axial direction. The distal end is provided with a plurality of support rods arranged at intervals in a circumferential direction of the tube and having relative converged and flared configurations. More than two connecting strips are provided in the axial direction between two adjacent support rods, and each connecting strip is folded back and forth in the converged configuration and tends to be straightened in the flared configuration relative to the converged configuration. The straightened lengths of the connecting strips increase sequentially from the proximal end to the distal end. Two ends of each connecting strip are connected to the support rods on the corresponding sides and the connecting portions have the same axial level.

In the following, several alternatives are provided, but merely as further additions or preferences, instead of as additional limitations to the above-mentioned technical solution. Without technical or logical contradiction, the alternatives can be combined with the above-mentioned technical solution, individually or in combination.

Optionally, 3 to 4 connecting strips are provided in the axial direction between two adjacent support rods.

Optionally, the two ends of each connecting strip are connecting ends, and the connecting ends are located at a distal side or a proximal side of the connecting strip in the axial direction.

Optionally, the support rod extends with equal width in the axial direction, and the connecting strip has a smooth transition at a turning portion.

Optionally, the connecting strips are similar in shape.

Optionally, the connecting strip is approximately W-shaped, and the two ends thereof are turned outwards to connect with the supporting rods on the corresponding sides.

Optionally, the connecting strip includes a peak and a valley, and the peak and the valley face towards the axial direction of the expansion section.

Optionally, the two ends of the most distal connecting strip are tangent to distal ends of the respective supporting rods on the corresponding sides.

Optionally, axial spans of the connecting strips increase sequentially from the proximal end to the distal end.

Optionally, from the proximal end to the distal end, a ratio of the axial span of one connecting strip to that of an adjacent connecting strip is 1:1.2 to 2, for example 1:1.4.

Optionally, a ratio of the axial span of the most proximal connecting strip to that of the most distal connecting strip is 1:2 to 4, for example 1:2.8.

Optionally, an area where the support rods are located is defined as an expansion section of the tube, and a section of the tube adjacent to a proximal end of the expansion section has a metal reinforcement layer, the metal reinforcement layer is a metal tube with a hollow structure, and the support rods, the connecting strips and the metal tube are formed in one piece.

Optionally, the tube further includes a middle section located at the proximal end of the expansion section, and the middle section is more readily flexible than the expansion section.

Optionally, both inner and outer sides of the metal reinforcement layer are provided with polymer covering film layers, and the inner and outer polymer covering film layers extend distally and past the expansion section and are connected with each other at the distal end to form a protective section.

The disclosure further provides a delivery system, including:
 a catheter assembly including the sheath for loading and retracting a prosthetic implant as described above and an inner shaft assembly, and the prosthetic implant is connected to a distal end of the inner shaft assembly; and
 a control handle, a proximal end of the catheter assembly is connected to the control handle.

During the retraction, the support rods of the sheath according to the present disclosure are subjected to different pulling forces from the respective connecting strips so as to turn outwardly in a curve form, which facilitates the retraction of the prosthetic implant. In the flared configuration, the expansion section of the support rods with a strong structural strength and the flared opening facilitate the retraction of the prosthetic implant and prevent the prosthetic implant from being damaged, improving the success rate of the surgery.

Figure 1:
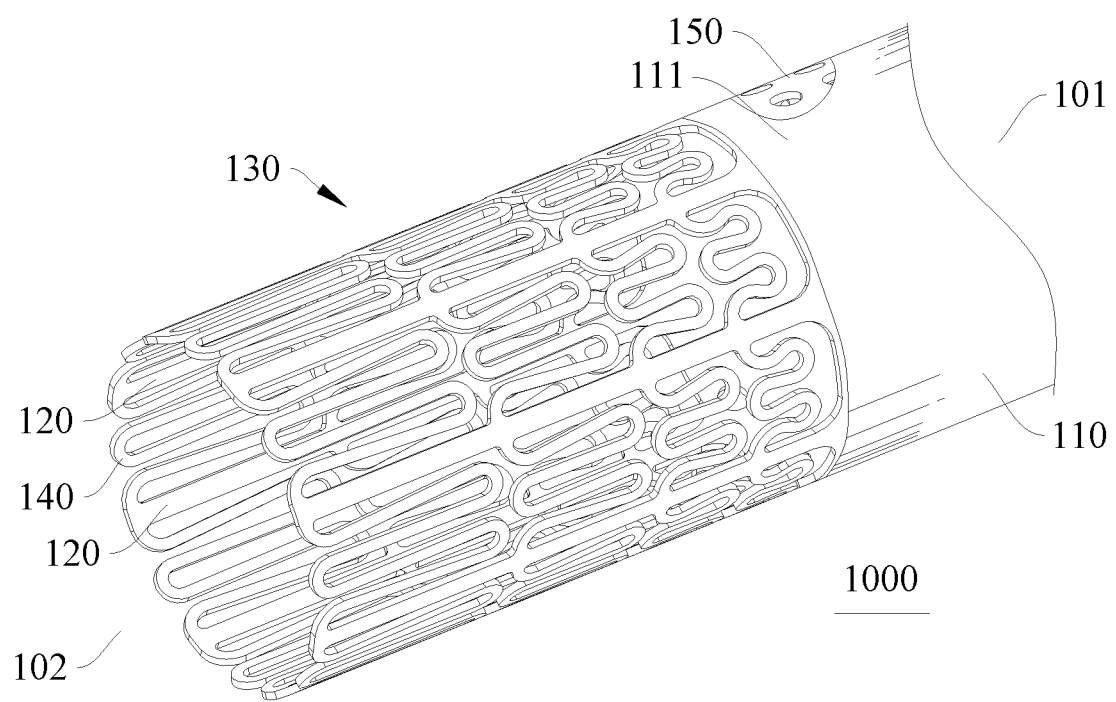
FIG. 1 is a schematic structural view of part of a sheath according to an embodiment of the present disclosure in a converged configuration (a polymer covering film layer is not shown on an expansion section)

LIST OF REFERENCE SIGNS 1000, sheath; 101, proximal end; 102, distal end;
110, tube; 111, polymer covering film layer; 112, protective section;
120, support rod; 122, connecting portion; 130, expansion section; 140, connecting strip; 140a, first connecting strip; 140b, second connecting strip;
140c, third connecting strip; 140d, fourth connecting strip; 141, first segment; 142, second segment; 143, third segment; 144, fourth segment; 145, connecting end; 145a, first connecting end; 145b, second connecting end; 146, turning portion; 147, peak; 148, valley; 147a, first peak; 148a, first valley; 148b, second valley;
150, metal reinforcement layer; 190, middle section;
2000, delivery system; 210, catheter assembly; 220, control handle; 230, inner shaft assembly;
3, prosthetic implant.

DESCRIPTION OF EMBODIMENTS

The technical solutions according to the embodiments of the present disclosure will be described clearly and fully in combination with the drawings according to the embodiments of the present disclosure. Obviously, the described embodiments are not all embodiments of the present disclosure, but only part of the embodiments of the present disclosure. Based on the disclosed embodiments, all other embodiments obtained by those skilled in the art without creative work fall into the scope of this invention.

It should be noted that, when a component is "connected" with another component, it may be directly connected to another component or may be indirectly connected to another component through a further component. When a component is "provided" on another component, it may be directly provided on another component or may be provided on another component through a further component.

Unless otherwise defined, all technical and scientific terms used herein have the same meaning as commonly understood by a person skilled in the art. The terms in the description of the present disclosure are used to describe specific embodiments, and not to limit the present disclosure. The term "and/or" used herein includes one or more of the listed options in any combinations, or the combination of all of the listed options.

In the present disclosure, the terms "first", "second" and the like are used for descriptive purposes only and are not to be understood as indicating or implying the relative importance or the number or order of the technical features referred. Thus, features defined with "first", "second" can explicitly or implicitly include one or more of such features. In the description of the present invention, "plurality" means at least two, such as two, three, etc., unless explicitly and specifically defined otherwise.

In the following drawings or descriptions, the prosthetic implant uses a prosthetic heart valve as an example. The prosthetic heart valve generally includes a deformable stent and leaflets connected within the stent. The stent is generally cylindrical, and the side wall thereof has a hollow meshed structure. Unless otherwise specified, the shape or size of the meshed structure is not strictly limited. The interior of the stent is a blood flow channel, and the leaflets cooperate with each other to open and control the blood flow channel within the stent. For positioning in the human body, the stent can be provided with positioning structures at the periphery, such as anchors, arms, and the like, that can engage with the surrounding native tissue.

The stent can be controlled by a wire, so that it can be retracted as desired during the release process. The stent can be formed by cutting a tube or braiding wires, and the leaflets can be connected to the stent by sewing, bonding or molding.

The stent generally has a connecting structure for engaging with the catheter assembly to limit each other, thereby preventing undesired deflection during delivery. The prosthetic implant has a radially compressed configuration during the interventional delivery, i.e., a loaded state, and a released state after being released from the catheter assembly and radially expanded in the human body.

For direction reference, the proximal end herein generally refers to the side adjacent to the operator (such as the physician), and the distal end refers to the side that is relatively far away from the operator. Each component has its own opposing distal and proximal ends in the intervention path. In theory, when the catheter assembly and the control handle are completely straightened, the straight line between the proximal end and the distal end defines the axis and thus the axial direction, and then the radial direction perpendicular to the axial direction and the circumferential direction around the axial direction can be determined. For structure reference, "end" herein refers to an end face of the structure or a certain point or a certain area at the corresponding side or a specific structure connected to the point or the area.

Figure 2:
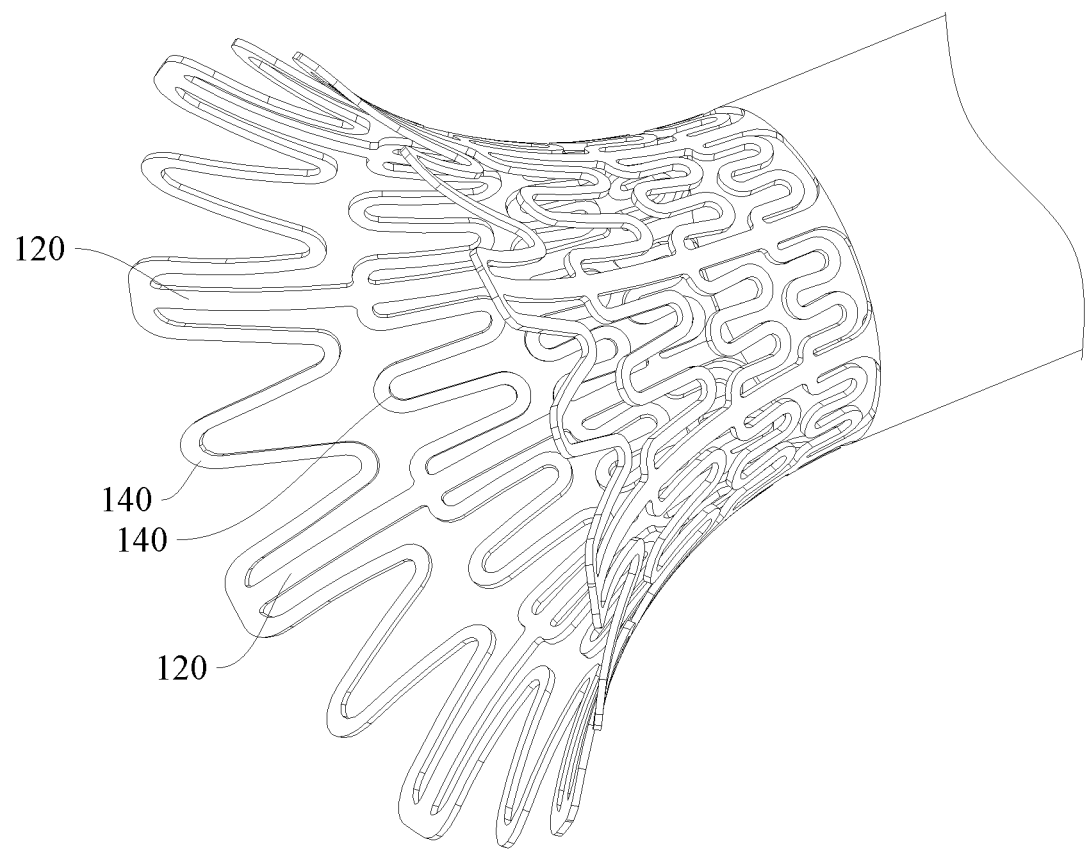
FIG. 2 is a schematic structural view of part of the sheath in FIG. 1 with the expansion section in a flared configuration.
Figure 3:
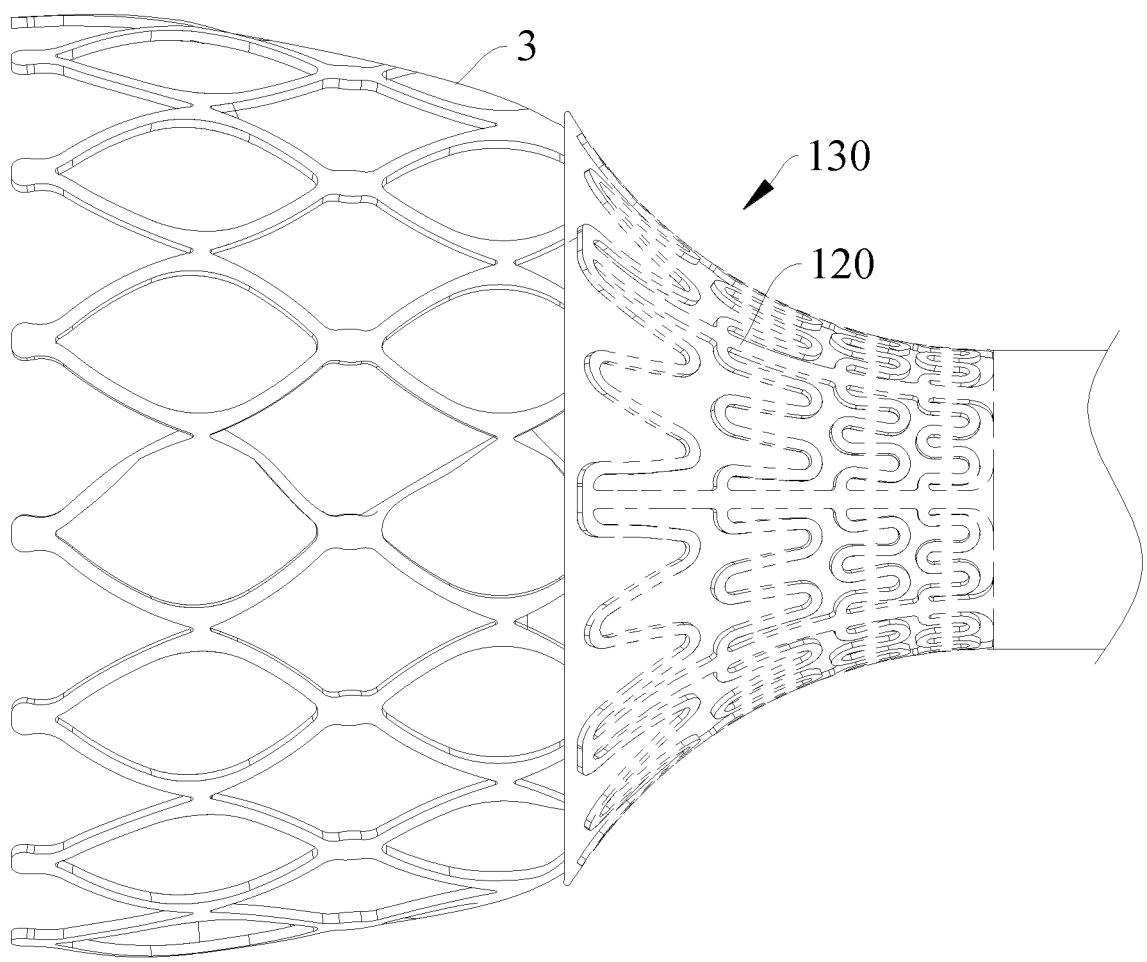
FIG. 3 is a schematic structural view of part of the sheath according to an embodiment of the present disclosure retracting a prosthetic implant.

As shown in FIGS. 1 to 5, the present disclosure provides a sheath 1000 (hereinafter, sheath) for loading and retracting a prosthetic implant. The sheath includes a tube 110, and the tube 110 has opposing distal and proximal ends 102 and 101 in its axial direction. The distal end 102 includes a plurality of support rods 120 arranged at intervals in the circumferential direction of the tube. The support rods 120 have relatively converged and flared configurations, which two configurations mainly differ in the radial deformation of the support rods relative to the axis of the tube. In the axial direction of the tube, the support rods 120, as a whole, is configured as an expansion section 130. As shown in FIG. 1, the expansion section 130 has a straight cylindrical shape in the converged configuration. As shown in FIG. 2, in the flared configuration, the portions of the expansion section 130 in the axial direction are away from the axis of the tube. As shown in FIG. 3, when being retracted, the prosthetic implant acts on the distal end of the sheath 1000, thereby driving the expansion section 130 to transform from the converged configuration to the flared configuration.

More than two connecting strips 140 are arranged in the axial direction between two adjacent support rods 120. Each connecting strip 140 is folded back and forth in the converged configuration, and tends to be straightened in the flared configuration relative to the converged configuration. In the flared configuration, the connecting strips 140 pull adjacent support rods 120 towards each other, thereby preventing the support rods 120 from being further flared. From the proximal end to the distal end, the straightened lengths of the connecting strips 140, i.e., the lengths along their own extension paths, increase sequentially. The two ends of each connecting strip 140 are connected to the supporting rods 120 on the corresponding sides, and the connecting portions have the same axial level. Different pulling forces are provided at different portions of the tube in the axial direction, i.e., the corresponding connecting portions, so that the support rods 120 assume arcs in the flared configuration, and thus the expansion section assumes a flared configuration, which improves the smoothness of retracting the prosthetic implant.

As the connecting portions of each connecting strip 140 with the supporting rods 120 on two sides have the same axial level, adjacent supporting rods 120 are subjected to the same force at the respective axial levels, and thus two adjacent supporting rods 120 have the same radian.

In the converged configuration, folding back and forth means, in the axial direction of the tube, extending from the support rod, for example, towards the distal or proximal end, and then back towards the proximal or distal end, which process is defined as folding back and forth once. In some embodiments, the folding back and forth occurs at least once.

The connecting strips folded back and forth facilitate the flare of the expansion section 130. Further, the connecting strips are arranged within the gap between adjacent support rods 120 to ensure the structural strength of the expansion section, facilitating the interventional delivery in the human body in the converged configuration, and maintaining in a stable attitude with a flared opening in the flared configuration to improve the efficiency of retracting the prosthetic implant and avoid damage to the sheath by the prosthetic implant.

In the axial direction, the variation of the straightened lengths of the connecting strips can adapt to the gradual increase of the deformation degrees of the support rods in the axial direction.

From the proximal end to the distal end, the straightened lengths of the connecting strips 140 increase sequentially by means of: in the converged configuration, folding the connecting strips different times, or providing connecting strips with different lengths in the axial direction, or both.

For the convenience of description, a group of connecting strips in the following refers to all connecting strips between two adjacent support rods, and a pair of connecting strips refers to two connecting strips that are located on two sides of one supporting rod and roughly at the same axial level.

Figure 4:
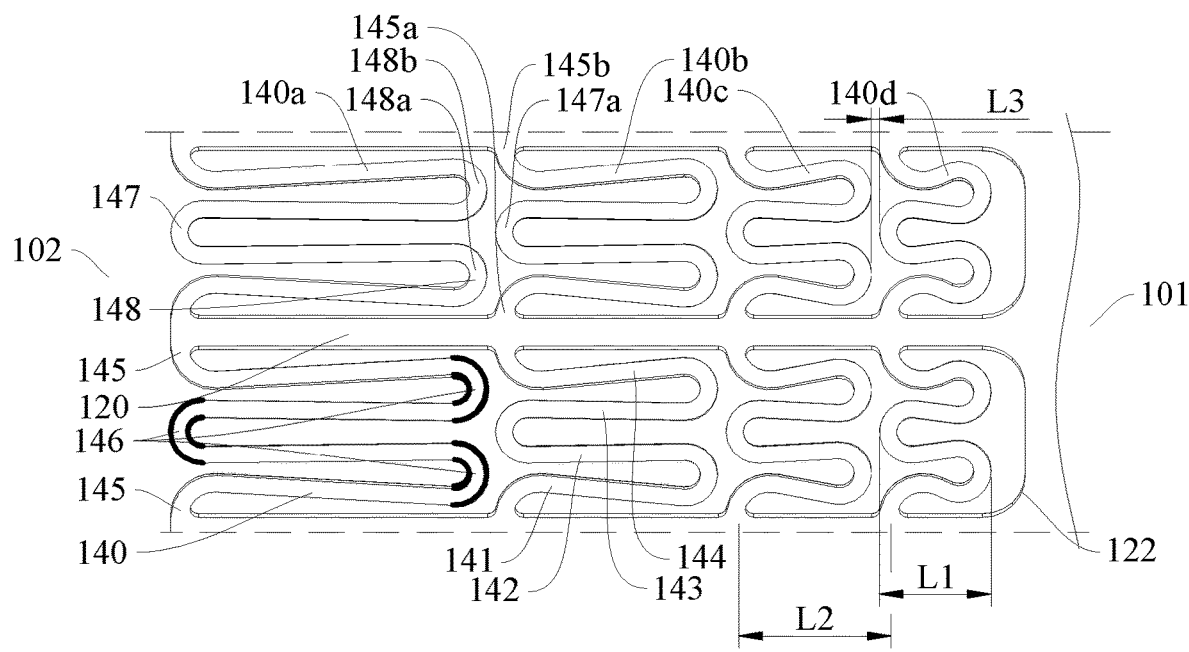
FIG. 4 is a schematic structural view of part of the sheath according to an embodiment of the present disclosure in the converged configuration.

In this embodiment, four connecting strips 140 are arranged between two adjacent support rods 120 in the axial direction of the tube, i.e., a first connecting strip 140a, a second connecting strip 140b, a third connecting strip 140c and a fourth connecting strip 140d from the proximal end to the distal end. Each connecting strip is folded back and forth circumferentially in the converged configuration (unexpanded state), and the two ends of each connecting strip having a tendency to be straightened move far away from each other in the flared configuration (expanded state) relative to the converged configuration. From the proximal end to the distal end, the straightened lengths of the connecting strips increase sequentially. The two ends of each connecting strip are connected with the support rods 120 on the corresponding sides and the connecting portions have the same axial level. As shown in FIG. 4, the two ends of a single connecting strip 140, i.e., the connecting ends 145, are respectively connected to the supporting rods 120 on the corresponding sides, and the connecting ends 145 have the same axial level.

The connecting strip 140 has a peak 147 and a valley 148, wherein the peak 147 and valley 148 face towards the axial direction of the expansion section 130, and the peak 147 is located distally from the valley 148. The numbers of peak(s) 147 and valley(s) 148 vary depending on the times the connecting strip is folded back and forth. The peaks 147 of the first connecting strips 140a at the most distal end of the expansion section are located on the same first circumference (in the axial direction of the tube); the valleys 148 of the first connecting strips 140a at the most distal end of the expansion section are located on the same second circumference, and the second circumference is parallel to the first circumference. In this embodiment, the ends of the first connecting strips 140a and the peaks 147 of the first connecting strips 140a are located on the same circumference. It should be noted that, the connecting ends of the connecting strips 140 with the supporting rods 120 are on the same circumference where the peaks or valleys are located, but are not considered as the peaks or valleys.

Figure 6:
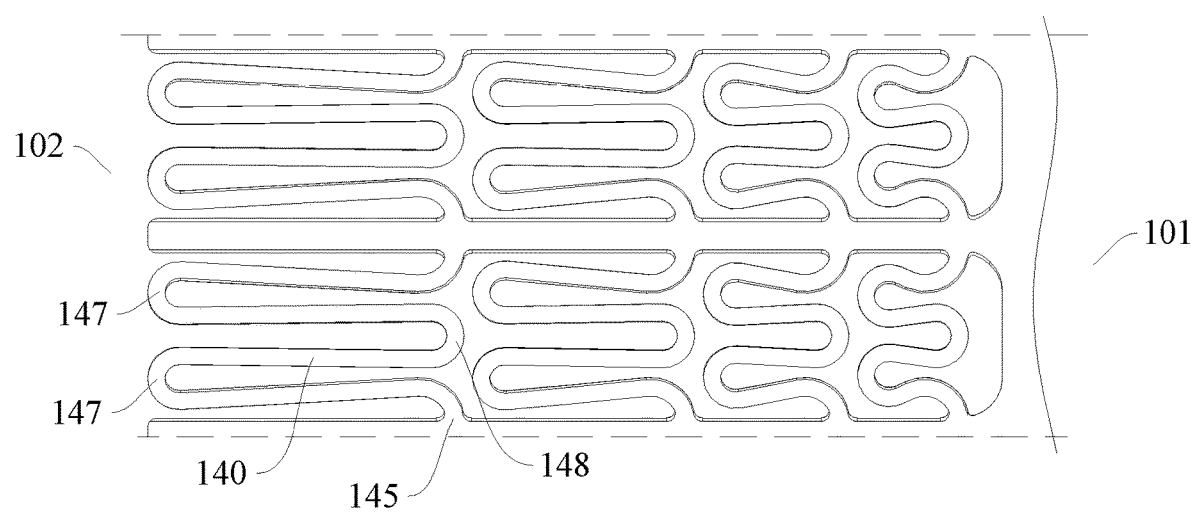
FIG. 6 is a schematic structural view of part of a sheath according to another embodiment of the present disclosure in a converged configuration.

The second connecting strip 140b, the third connecting strip 140c and the fourth connecting strip 140d each have a shape similar to that of the first connecting strip 140a. The number of peak(s) and valley(s) between the two ends of the second connecting strip 140b, the third connecting strip 140c or the fourth connecting strip 140d is the same as that of peak(s) and valley(s) between the two ends of the first connecting strip 140a. For example, the connecting strip is approximately W-shaped, i.e., folded back and forth three times. In one embodiment, as shown in FIG. 4, there is one peak 147 and two valleys 148 for each connecting strip. In another embodiment, as shown in FIG. 6, there are two peaks 147 and one valley 148 for each connecting strip 140.

The peaks and valleys of the first connecting strip 140a, the second connecting strip 140b, the third connecting strip 140c and the fourth connecting strip 140d are arranged alternately in the axial direction. Taking the first connecting strip 140a and the second connecting strip 140b in FIG. 4 as an example, in the converged configuration, the first valley 148a of the first connecting strip 140a is located between the first connecting end 145a and the first peak 147a of the second connecting strip 140b. The peak 147 of the second connecting strip 140b is located between the first valley 148a and the second valley 148b of the first connecting strip 140a. The second valley 148b of the first connecting strip 140a is located between the second connecting end 145b and the first peak 147a of the second connecting strip 140b.

In some other embodiments, two to three connecting strips 140 are arranged between two adjacent support rods 120 in the axial direction of the tube.

In one embodiment, two ends of each connecting strip 140 are connecting ends 145, and the connecting ends 145 are located at the distal side of the connecting strip 140 in the axial direction. The deformation of the expansion section 130 gradually increases from the proximal end to the distal end. The connecting ends 145, as force bearing points, are arranged at the distal side of the connecting strip 140, so as to better adapt to the deformation of the expansion section 130 and reduce the risk of tearing the inner and outer covering films (i.e., the polymer covering film layers described below) on the expansion section. For each support rod 120, the connecting strips 140 on two sides in the circumferential direction are arranged symmetrically.

For example, as shown in FIG. 6, in another embodiment, two ends of each connecting strip 140 are connecting ends 145, and the connecting ends 145 are located on the proximal side of the connecting strip 140 in the axial direction.

In one embodiment, the support rod 120 extends with equal width in the axial direction, and the connecting strip 140 has a smooth transition at the turning portion 146, reducing the stress change of the deforming connecting strip 140 during the flare process. The connecting strip 140 extends with equal width, and the ratio of the width of the connecting strip 140 to the width of the support rod 120 is 1:1.5 to 2.5, preferably 1:1.7. The peak 147 and the valley 148 are located at the turning portions 146.

In one embodiment, the connecting strips 140 are similar in shape. Being similar in shape means that the times of folding the connecting strips 140 back and forth are the same and the extension directions are the same among others. For example, the aforementioned connecting strips 140 are approximately W-shaped. By contrast, with a V-shape folded back and forth once, under the same deformation, the connecting strip exerts a more concentrated stress on the covering films, which increases the risk of tearing the covering films. However, the W-shaped structure can distribute the deformation stress on multiple portions in the circumferential direction more evenly, so that the stress acting on the inner and outer covering films are dispersed more broadly and uniformly, reducing the risk of tearing the covering films.

On the other hand, if the connecting strip is folded too much times, the width of the connecting strip has to be reduced to adapt to the limited space (the space between two support rods), reducing the structural strength of the connecting strip, so that the connecting strip would be easy to warp and damage the covering films during the flare process, affecting the retract of the prosthetic implant.

The two ends of the W-shaped connecting strip 140 are turned outward in the circumferential direction of the tube and connected with the supporting rods 120 on the corresponding sides (the connecting portion is the connecting end 145). The connecting end 145 is substantially perpendicular to the support rod 120, with a reliable force, so that the support rod 120 will not be twisted to tear the polymer covering film layers during the deformation process.

For each connecting strip 140, the distal turning portion 146 and the connecting ends 145 are at the same axial level, and the two proximal turning portions 146 are at the same axial level.

In one embodiment, as shown in FIG. 4, in the converged configuration, for each group of connecting strips, the axial spans L1 of the connecting strips 140 increase sequentially from the proximal end to the distal end. The axial span of the connecting strip is defined as the axial linear distance from the proximal end to the distal end of the connecting strip itself.

In one embodiment, the distances L2 between the corresponding connecting ends 145 of each two adjacent connecting strips 140 gradually increase from the proximal end to the distal end.

In one embodiment, within two adjacent connecting strips, the axial distance between the distal end of the proximal connecting strip and the proximal end of the distal connecting strip is L3. For example, as shown in FIG. 4, the axial distance between the distal end of the fourth connecting strip 140d and the proximal end of the third connecting strip is L3. For each group of connecting strips, L3 is approximately the same.

For example, from the proximal end to the distal end, the ratio of the axial span of a connecting strip to that of an adjacent connecting strip 140 is 1:1.2 to 2, preferably 1:1.4. The ratio of the axial span of the most proximal connecting strip to the axial span of the most distal connecting strip 140 is 1:2 to 4, preferably 1:2.8.

Figure 5:
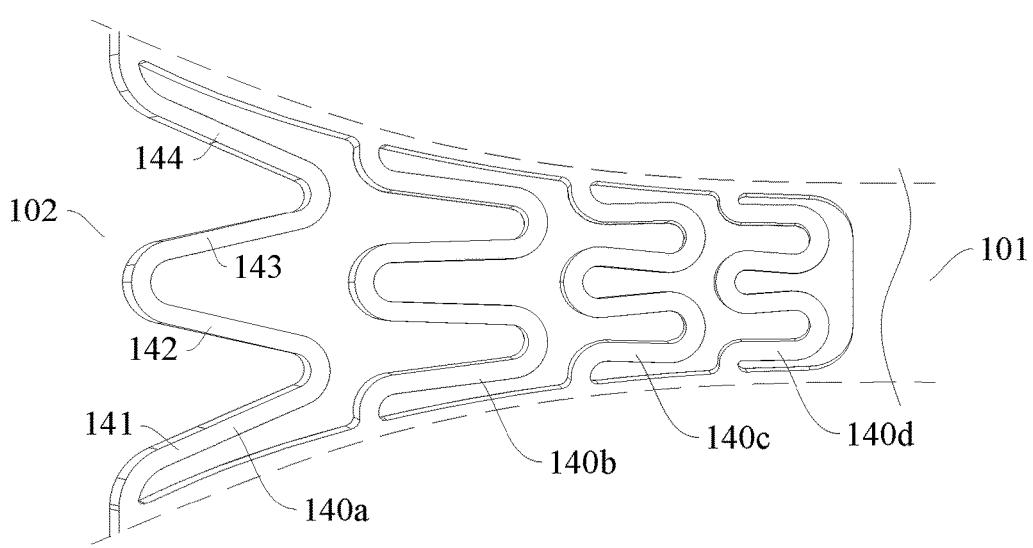
FIG. 5 is a schematic structural view of FIG. 4 when the sheath is in the flared configuration.

As shown in FIG. 4 and FIG. 5, the connecting strip 140 includes a first segment 141, a second segment 142, a third segment 143 and a fourth segment 144 which are successively connected in the circumferential direction. In the converged configuration, two adjacent segments of each connecting strip together assume an approximately Ω-shape. In the flared configuration, for the distal two connecting strips 140a and 140b, two adjacent segments assume an approximately V-shape, and for the two proximal connecting strips 140c and 140d, two adjacent segments still assume an approximately Ω-shape.

In one embodiment, the two ends of the most distal connecting strip 140 are tangent to the distal ends of the supporting rods 120 on the corresponding sides, respectively, so as to increase the structural strength of the distal ends of the supporting rods and the contact areas thereof with the prosthetic implant. It can be concluded from the foregoing that the turning portions 146 at the distal ends of the connecting strips are at the same axial level as the connecting ends 145, that is, the turning portions 146 function as the distal end of the expansion section 130, which facilitates the retraction.

In one embodiment, the section of the tube 110 adjacent to the proximal end of the expansion section has a metal reinforcement layer 150. The metal reinforcement layer 150 is a metal tube with a hollow structure, which is formed in one piece with the support rods 120 and the connecting strips 140, for example, by cutting a tube. As shown in FIG. 4, the support rods 120 are connected with the metal tube, and the connecting portions 122 of the two are chamfered. When retracting the prosthetic implant, the section with the metal reinforcement layer 150 is not flared.

The metal tube is connected with the expansion section 130 and the length of the metal tube is not strictly limited. For example, the axially proximal end of the metal tube can be located at the proximal side of the end of the prosthetic implant that is compressed in the tube.

In one embodiment, the tube 110 further includes a middle section 190 located at the proximal end of the expansion section. The middle section 190 is more readily flexible than the expansion section 130, which facilitates passing through the curved portion in the human body, such as the aortic arch.

Figure 7:
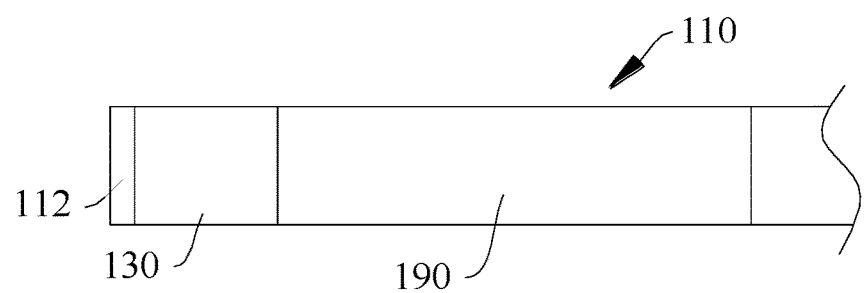
FIG. 7 is a schematic structural view of a distal end of the sheath according to an embodiment of the present disclosure.

Both inner and outer sides of the metal reinforcement layer 150 are provided with polymer covering film layers 111. The polymer covering film layer 111 is made of a transparent or opaque material. For convenience of observation, the polymer covering film layer in FIG. 1 is shown in an opaque form. As shown in FIG. 7, the polymer covering film layer 111 extends to the distal end to cover the expansion section 130, and the inner and outer polymer covering film layers 111 meet and connect with each other, for example, by fuse, at the distal end to form a protective section 112, which improves the connection strength of the inner and the outer polymer covering film layers and covers the expansion section better, reducing the risk of tissue damage during the intervention of the sheath.

Figure 8:
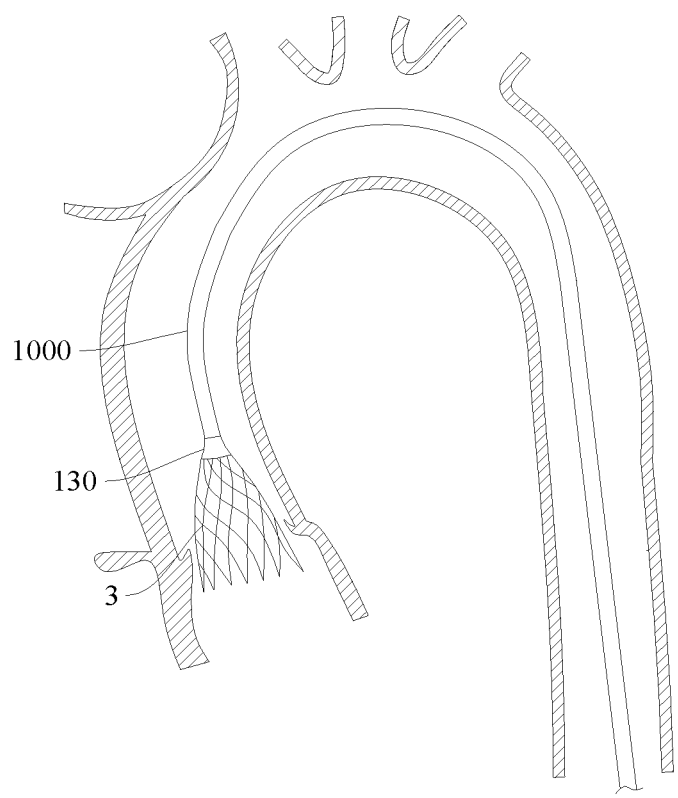
FIG. 8 is a schematic structural view of the sheath according to an embodiment of the present disclosure retracting a prosthetic implant in the human body.
Figure 9:
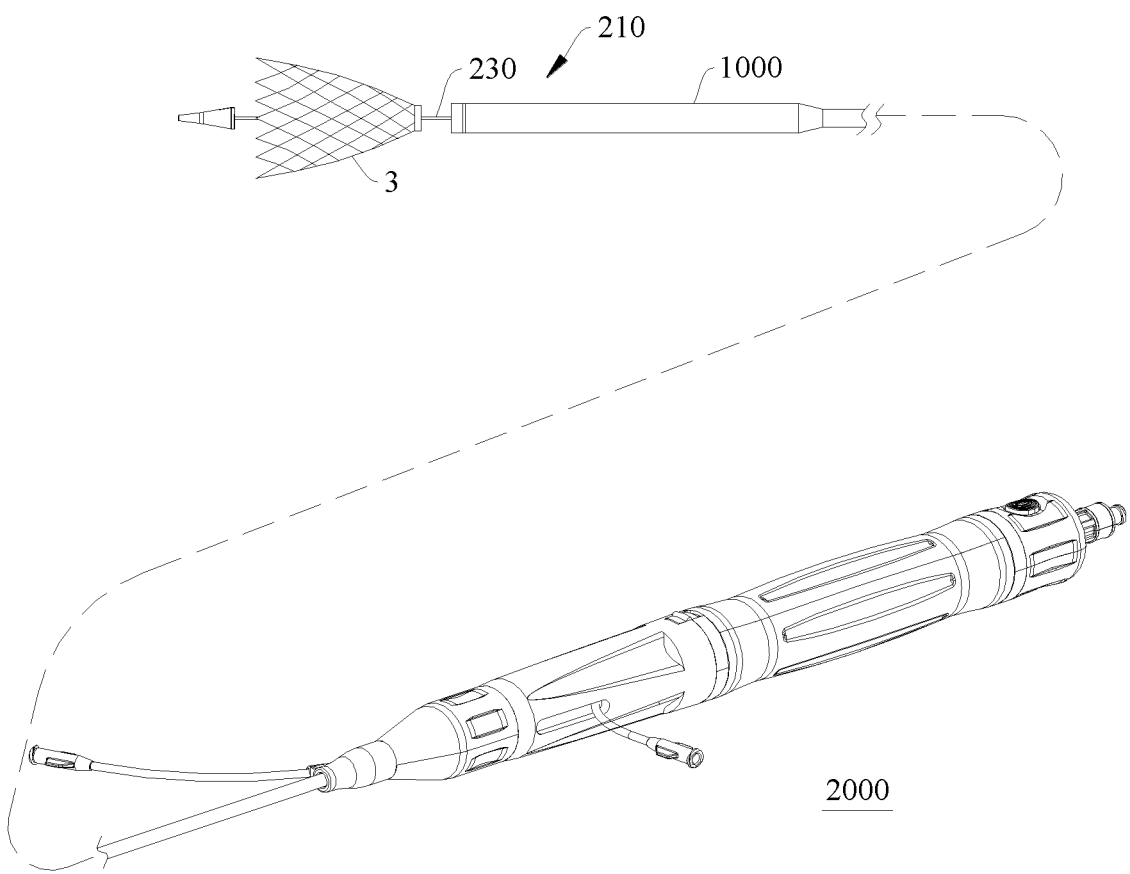
FIG. 9 is a schematic structural diagram of a delivery system according to an embodiment of the present disclosure.

As shown in FIGS. 8 and 9, the present disclosure further provides a delivery system 2000, including a catheter assembly 210 and a control handle 220. The catheter assembly 210 includes the sheath 1000 according to the above-mentioned embodiments and an inner shaft assembly 230. The prosthetic implant is connected to the distal end of the inner shaft assembly 230. The sheath 1000 has an initial state of covering the prosthetic implant, and a release state in which it is moved relative to the inner shaft assembly 230 so as to completely expose the prosthetic implant. The proximal end of the catheter assembly 210 is connected to the control handle 220. The specific structure of the catheter assembly and the control handle can use the existing techniques.

The retraction process is described in detail below:

The control handle 220 drives the sheath 1000 to move distally, so that the sheath 1000 moves axially relative to the inner shaft assembly 230, and the expansion section of the sheath acts on the prosthetic implant 3 until the prosthetic implant is completely retracted into the sheath During the retracting process, the support rods of the sheath according to the present disclosure are flared to assume arcs with the same radian, so that the inside of the expansion section is smooth without turning points, and thus the prosthetic implant can be compressed more smoothly. In the flared configuration, the expansion section with a strong structural strength and the flared opening facilitate the retraction of the prosthetic implant and prevent the prosthetic implant from being damaged, improving the success rate of the surgery.

The technical features of the above embodiments can be arbitrarily combined, and not all possible combinations of the technical features of the above embodiments have been described for the sake of brevity of description. However, as long as there is no contradiction in the combination of these technical characteristics, such combination should be regarded as falling into the scope of this specification. When the technical features in different embodiments are shown in the same drawing, it can be considered that the drawing also discloses a combined embodiment of various embodiments involved.

The above-described embodiments only illustrate several embodiments of the present disclosure, and the description thereof is specific and detail, but should not be construed as limiting the scope of the patent disclosure. It should be noted that, for those of ordinary skill in the art, several modifications and improvements can be made without departing from the concept of the present disclosure, all of which fall into the protection scope of the present disclosure.

The invention claimed is:

1. A sheath for loading and retracting a prosthetic implant, comprising a tube having opposing distal and proximal ends in its axial direction, the distal end being provided with a plurality of support rods arranged at intervals in a circumferential direction of the tube and having relative converged and flared configurations, wherein more than two connecting strips are provided in the axial direction between two adjacent support rods, and each connecting strip is approximately W-shaped and folded back and forth and two ends thereof are turned outwards to connect with the respective supporting rods at connection portions which have the same axial level; each connecting strip comprises a first segment, a second segment, a third segment and a fourth segment which are successively connected in the circumferential direction, and in the converged configuration, two adjacent segments of each connecting strip together assume an approximately Ω-shape; lengths of the connecting strips increase sequentially from the proximal end to the distal end; and wherein an area where the support rods are located is defined as an expansion section of the tube, and when being retracted, the prosthetic implant acts on the distal end of the sheath, thereby driving the expansion section to transform from the converged configuration to the flared configuration.

2. The sheath for loading and retracting a prosthetic implant according to claim 1, wherein 3 to 4 connecting strips are provided in the axial direction between two adjacent support rods.

3. The sheath for loading and retracting a prosthetic implant according to claim 1, wherein the connection portions of each connecting strip are located at a distal side of the connecting strip in the axial direction.

4. The sheath for loading and retracting a prosthetic implant according to claim 1, wherein each of the support rods extends with equal width in the axial direction, and each of the connecting strips has a smooth transition at a turning portion.

5. The sheath for loading and retracting a prosthetic implant according to claim 1, wherein the connecting strips are similar in shape.

6. The sheath for loading and retracting a prosthetic implant according to claim 5, wherein the two ends of the most distal connecting strip are tangent to distal ends of the respective supporting rods on the corresponding sides.

7. The sheath for loading and retracting a prosthetic implant according to claim 1, wherein axial spans of the connecting strips increase sequentially from the proximal end to the distal end.

8. The sheath for loading and retracting a prosthetic implant according to claim 7, wherein from the proximal end to the distal end, a ratio of the axial span of one connecting strip to that of an adjacent connecting strip is 1:1.2 to 2.

9. The sheath for loading and retracting a prosthetic implant according to claim 7, wherein a ratio of the axial span of the most proximal connecting strip to that of the most distal connecting strip is 1:2 to 4.

10. The sheath for loading and retracting a prosthetic implant according to claim 1, wherein a section of the tube adjacent to a proximal end of the expansion section has a metal reinforcement layer, the metal reinforcement layer is a metal tube with a hollow structure, and the support rods, the connecting strips and the metal tube are formed in one piece.

11. The sheath for loading and retracting a prosthetic implant according to claim 10, wherein the tube further comprises a middle section located at the proximal end of the expansion section, and the middle section is more readily flexible than the expansion section.

12. The sheath for loading and retracting a prosthetic implant according to claim 10, wherein both inner and outer sides of the metal reinforcement layer are provided with polymer covering film layers, and the inner and outer polymer covering film layers extend distally and past the expansion section and are connected with each other at the distal end to form a protective section.

13. A delivery system, comprising:
a catheter assembly comprising the sheath for loading and retracting a prosthetic implant according to claim 1 and an inner shaft assembly, the prosthetic implant being connected to a distal end of the inner shaft assembly; and
a control handle, a proximal end of the catheter assembly is connected to the control handle.

14. A medical system, comprising:
an expandable prosthetic implant;
a catheter assembly comprising a sheath for loading and retracting the prosthetic implant and an inner shaft assembly, wherein the prosthetic implant is connected to a distal end of the inner shaft assembly, and the sheath has an axial direction and a circumferential direction and comprises:
  a proximal section; and
  an expandable distal section connected to the proximal section, the expandable distal section having relative converged and flared configurations and comprising:
    a plurality of support rods arranged at intervals in the circumferential direction; and
    a plurality of connecting strips, wherein more than two connecting strips are provided in the axial direction between two adjacent support rods, and each connecting strip is approximately W-shaped and folded back and forth and two ends thereof are turned outwards to connect with the respective supporting rods at connection portions which have the same axial level; and
a control handle, wherein a proximal end of the catheter assembly is connected to the control handle, and the control handle is configured to drive the sheath to move distally to make the expandable distal section of the sheath act on the prosthetic implant that has already been at least partially expanded which in turn drives the expandable distal section to transform from the converged configuration to the flared configuration until the prosthetic implant is completely retracted and compressed into the sheath.

15. The medical system according to claim 14, wherein axial spans of the connecting strips increase sequentially from the proximal end to the distal end.

16. The medical system according to claim 15, wherein from the proximal end to the distal end, a ratio of the axial span of one connecting strip to that of an adjacent connecting strip is 1:1.2 to 2.

17. The medical system according to claim 15, wherein a ratio of the axial span of the most proximal connecting strip to that of the most distal connecting strip is 1:2 to 4.

18. The medical system according to claim 14, wherein the proximal section of the sheath comprises a metal reinforcement layer, the metal reinforcement layer is a metal tube with a hollow structure, and the support rods, the connecting strips and the metal tube are formed in one piece.

* * * * *